United States Patent
Broad et al.

(10) Patent No.: US 6,516,667 B1
(45) Date of Patent: Feb. 11, 2003

(54) ULTRASONIC HARMONIC SIGNAL ACQUISITION

(75) Inventors: Ronald W. Broad, Arlington, WA (US); Yiu-Hung David Lam, Mukilteo, WA (US); James R. Jago, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/520,706

(22) Filed: Mar. 7, 2000

(51) Int. Cl.⁷ .................................................. A61B 8/00
(52) U.S. Cl. .............................. 73/602; 73/625; 73/626; 73/628; 600/443; 600/447
(58) Field of Search ......................... 73/602, 624, 625, 73/626, 627, 628; 600/437, 440, 441, 443, 447, 454, 453, 458

(56) References Cited

U.S. PATENT DOCUMENTS

| 4,016,750 | A | | 4/1977 | Green ........................ 73/620 |
| 5,833,613 | A | | 11/1998 | Averkiou et al. ............ 600/440 |
| 5,833,614 | A | * | 11/1998 | Dodd et al. .................. 600/447 |
| 5,879,303 | A | | 3/1999 | Averkiou et al. ............ 600/447 |
| 5,908,389 | A | * | 6/1999 | Roundhill et al. ........... 600/443 |
| 6,023,977 | A | * | 2/2000 | Langdon et al. .............. 367/87 |
| 6,146,330 | A | * | 11/2000 | Tujino et al. ................ 600/443 |
| 6,206,833 | B1 | * | 3/2001 | Christopher ................. 600/443 |

FOREIGN PATENT DOCUMENTS

| JP | 08294487 A | * | 11/1996 | ............ A61B/8/00 |
| WO | WO 99/08600 | * | 2/1999 | .................. 600/437 |

* cited by examiner

*Primary Examiner*—Hezron Williams
*Assistant Examiner*—Rose M. Miller
(74) *Attorney, Agent, or Firm*—W. Brinton Yorks, Jr.

(57) ABSTRACT

An ultrasonic diagnostic imaging system receives echo signals from a transducer for digital processing and image formation. An analog to digital converter converts the analog echo signals to digital signal samples. The dynamic range of the analog to digital converter is more efficiently used for harmonic imaging and saturation of the analog to digital converter is more effectively prevented by attenuating the fundamental signal content of echo signals prior to analog to digital conversion.

23 Claims, 4 Drawing Sheets

ULTRASONIC HARMONIC SIGNAL ACQUISITION

This invention relates to ultrasonic diagnostic imaging systems and, in particular, to ultrasonic diagnostic imaging systems which produce images of acquired harmonic signals.

The use of ultrasonic signals which are harmonically related to transmitted ultrasound signals for ultrasonic diagnostic imaging is described in U.S. Pat. No. 5,833,613 (Averkiou et al.) and U.S. Pat. No. 5,879,303 (Averkiou et al.) The '613 patent describes a number of techniques for imaging with harmonic contrast agents. Ultrasonic contrast agents are comprised of tiny encapsulated microbubbles which, when struck by a transmitted ultrasound wave, will exhibit nonlinear resonance, including resonance at harmonic frequencies of the transmitted wave frequency. This nonlinear resonance will return an echo signal containing the harmonic frequencies in addition to components at the fundamental (transmit) frequency. While the harmonic components are not as great in intensity as the fundamental components, they are nonetheless of relatively significant intensity and can be readily detected and discriminated to provide segmented contrast signal information.

The '303 patent describes another form of ultrasonic harmonic imaging known as tissue harmonic imaging. Tissue harmonic imaging relies upon the distortion of a transmitted wave which occurs as the wave passes through the tissue of the body. This distortion gives rise to nonlinear signal components including those at harmonics of the fundamental transmit frequency. The tissue harmonic signal components are of a lesser relative intensity as compared to contrast harmonic signal components, but may nonetheless be readily detected and used to form ultrasonic images. As explained in the '303 patent, tissue harmonic imaging prevents the occurrence of nearfield and other image artifacts which are common to fundamental signal images.

In both contrast and tissue harmonic imaging it is necessary to distinguish or separate the harmonic signal components from the accompanying fundamental frequency components. Efforts to effect this separation have focused on filtering techniques such as bandpass filtering, and signal processing techniques such as the multiple echo technique known as pulse inversion. However, all of these techniques can be impeded by limitations in signal acquisition, the apparatus and processing used to initially acquire the harmonic signals. One such limitation is inherent in the use of digital beamforming, which is in widespread use in virtually all of today's premium ultrasound systems. The initial step in digital beamforming is the digital sampling of received echo signals by analog to digital conversion. Since the harmonic components are many dB down from fundamental signal component amplitudes, particularly in the case of tissue harmonic signals, much of the dynamic range of the digital echo samples will be occupied by fundamental signal information. The fundamental signal components can even be of a strength which overwhelms or saturates the analog to digital converter, thereby rendering the harmonic components undetectable in subsequent harmonic discrimination or separation processing. Moreover, saturation will generate odd harmonics which can fall at even harmonic frequencies of interest, which is particularly troublesome in broadband imaging systems. It would be desirable to prevent such saturation and inability to detect the harmonic signal components. It would further be desirable to use a significant portion of the dynamic range of the analog to digital converter for conversion of the harmonic signal components.

In accordance with the principles of the present invention, the fundamental frequency components of an echo signal are selectively attenuated prior to digitization of the echo signal. In one embodiment one or more of a plurality of filter circuits are selectively switched into use prior to the analog to digital converter to attenuate fundamental frequency signal components. In another embodiment the characteristic of a programmable filter circuit is varied during receipt of echo signals in correspondence with depth dependent frequency attenuation. In yet another embodiment a plurality of filter circuits are sequentially switched into use to track the depth dependent changes of the echo signal.

Figure 1:
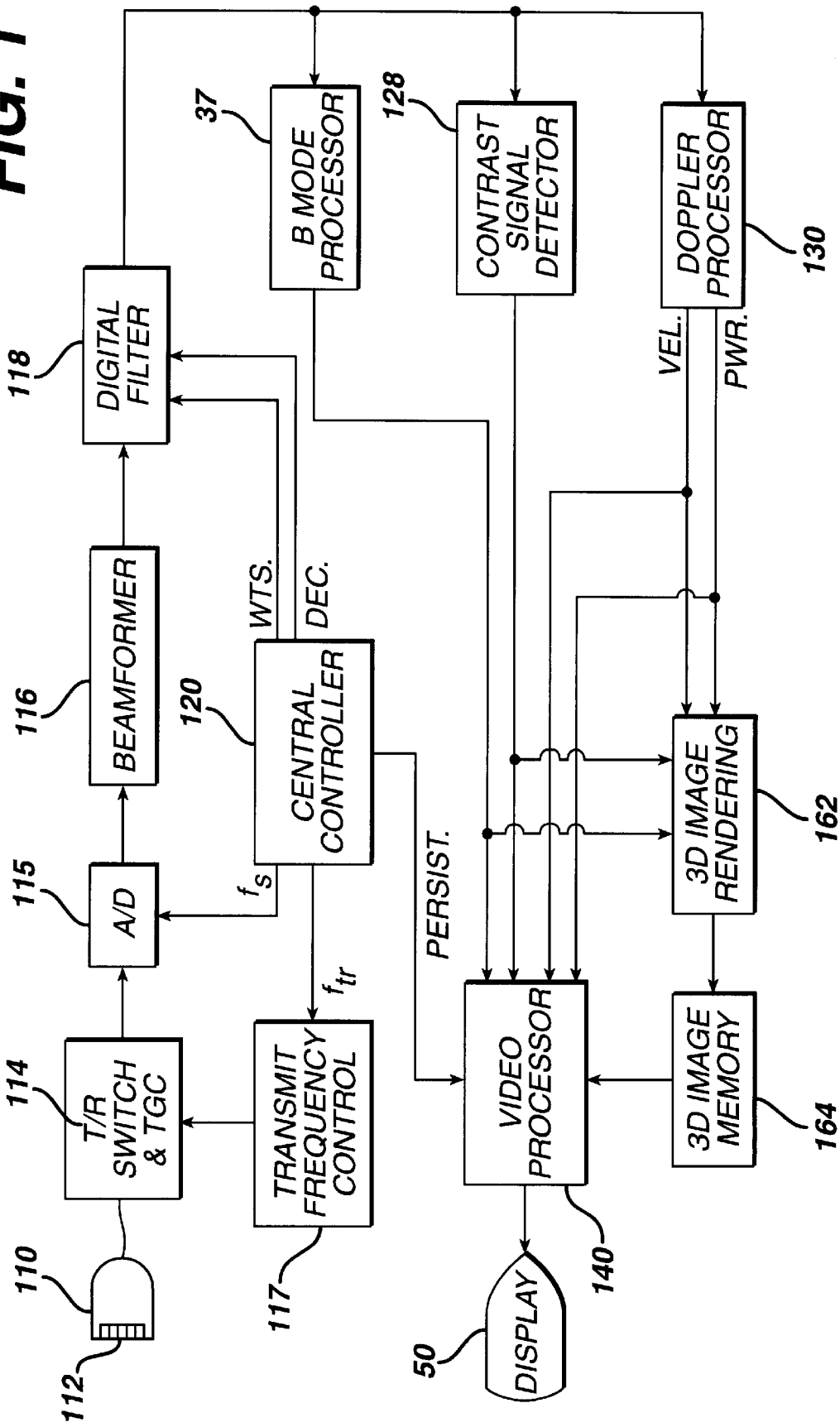
FIG. 1 illustrates in block diagram form an ultrasonic harmonic imaging system constructed in accordance with the principles of the present invention.

Referring first to FIG. 1, an ultrasonic imaging system for harmonic imaging is shown in block diagram form. A central controller 120 commands a transmit frequency control 117 to transmit a desired transmit frequency band. The parameters of the transmit frequency band, ftr, are coupled to the transmit frequency control 117, which causes the transducer 112 of ultrasonic probe 110 to transmit ultrasonic waves in the fundamental frequency band. The array transducer 112 or the probe 110 transmits ultrasonic energy and receives echoes returned in response to this transmission. The response characteristic of the transducer can encompass one broad passband or two distinguishable passbands, one around the fundamental transmit frequency and another about a harmonic frequency in the received passband. For harmonic imaging, a broadband transducer having a passband encompassing both the transmitted fundamental and received harmonic passbands is preferred. In harmonic contrast imaging the echo signals returned from harmonic contrast agents include harmonics of the fundamental transmit band. In tissue harmonic imaging tissue and cells in the body alter the transmitted fundamental frequency signals during propagation and the returned echoes contain harmonic components of the originally transmitted fundamental frequency. In the embodiment of FIG. 1 these echoes are received by the transducer array 112, coupled through the T/R switch 114, compensated for depth dependent attenuation by time gain control (TGC), and digitized by analog to digital converters 115. The sampling frequency $f_s$ of the A/D converters 115 is controlled by the central controller. The desired sampling rate dictated by sampling theory is at least twice the highest frequency of the received passband. Sampling rates higher than the minimum requirement are preferable, such as 24, 32, or 40 MHz.

The echo signal samples from the individual transducer elements are delayed and summed by a beamformer 116 to form coherent echo signals. The digital coherent echo signals are then filtered by a digital filter 118. The digital filter 118 can bandpass filter the signals to separate signals of the desired harmonic passband, and can also shift the frequency band to a lower or baseband frequency range. A preferred filter can take the form of a multitap digital FIR filter which can also decimate the output data rate. The digital filter 118 can also separate harmonic and fundamental frequency components by combining spatially correlated echoes which have been produced by differently modulated transmit signals, a technique known as pulse inversion which is described in U.S. Pat. No. 5,951,478. A digital filter of either type can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence simply by changing the filter coefficients of an FIR filter or the sense in which multiple echoes are combined in pulse inversion.

The filtered echo signals from the tissue or contrast agent are processed by either a B mode processor 37, a contrast signal processor '28, or a Doppler processor 130 for display as a two dimensional ultrasonic image on the display 50. A preferred form for the contrast signal processor is the power motion imaging processor shown and described in U.S. Pat. No. 5,718,229. Details of harmonic Doppler processing are found in U.S. Pat. No. 6,036,643. Harmonic contrast and tissue harmonic signals may be processed for display by any of the three processors 37, 128 and 130, as may fundamental frequency signals. The outputs of these processors are coupled to a 3D image rendering processor 162 for the rendering of three dimensional images, which are stored in a 3D image memory 164. Three dimensional rendering may be performed as described in U.S. Pat. Nos. 5,720,291, 5,474,073 and 5,485,842. The signals from the contrast signal detector 128, the processors 37 and 130, and the three dimensional image signals are coupled to a video processor 140 where they may be selected for two or three dimensional display on an image display 50 as dictated by user selection.

Figure 2:
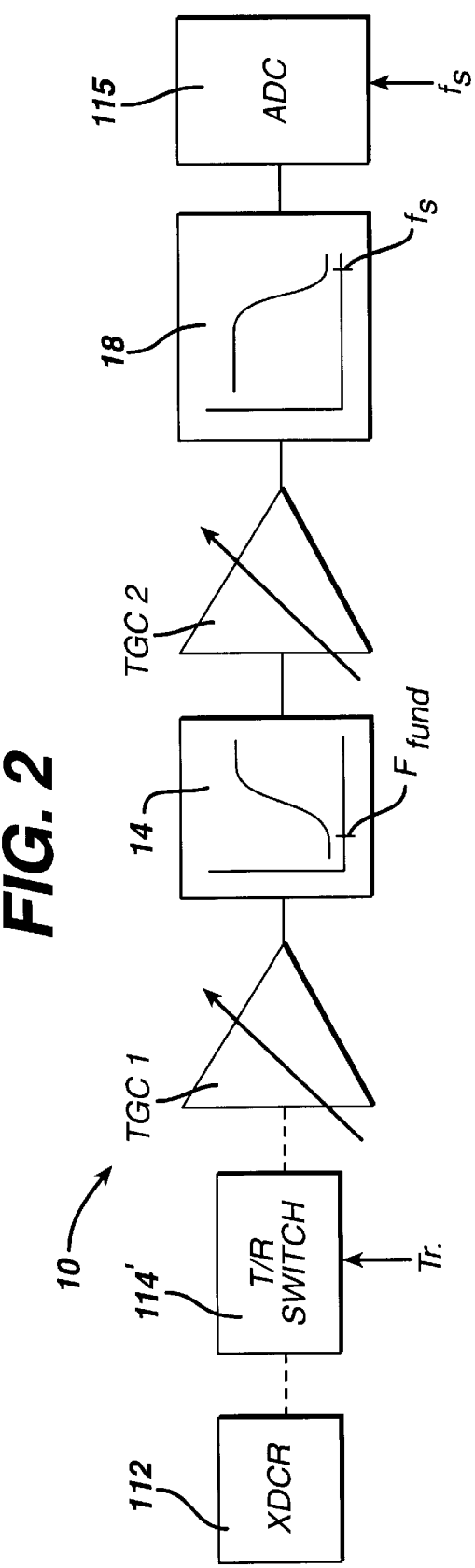
FIG. 2 illustrates in block diagram form the acquisition circuitry of an ultrasound beamformer channel constructed in accordance with the principles of the present invention.

An acquisition circuit 10 for a digital ultrasonic harmonic imaging system is shown in FIG. 2. The circuit 10 is preferably used between every element of the transducer 112 and the analog to digital converter (ADC) for that element. When the transducer is a single element (piston) transducer, only a single circuit 10 is required. For an array transducer 112, the circuit 10 is preferably employed between each element of the array following the T/R switch 114' and the ADC of the beamformer channel for the element. The illustrated acquisition circuit 10 includes a TGC (time gain compensation) circuit which applies variable gain or attenuation to the received echoes to offset the effects of depth dependent attenuation. TGC circuits are well known in the art and in general act to apply ever-increasing gain to the received echoes as echoes are received from ever-greater depths of the body. The preferred TGC circuit is a two stage circuit including circuits TGC 1 and TGC 2. The use of two circuits enables the use of two independently controlled gain characteristics which produce a composite effect on the received echo signals.

The gain controlled received echo signals are converted to digital signals by an analog to digital converter (ADC) 115. The echo signals are sampled at a rate determined by a sampling signal fs, which is chosen to sample the echo signals at a rate which satisfies the Nyquist criterion for the echo signal band. As mentioned above, the echo signals are sampled at a frequency which is at least twice the highest frequency of the received signal passband. The sampling rate is usually chosen in correspondence with the passbands of the transducers which are or are anticipated to be used with the ultrasound. system, and a suitable sampling frequency would be one which is a least twice the highest frequency received by the highest frequency transducer used. ADCs are commonly operated at sampling frequencies of 16, 24, 32 or 40 MHz. When the sampling signal causes the ADC to sample the received echo signal, the instantaneous amplitude of the echo signal is sampled and converted to a multibit digital value within the dynamic range of the number of bits used. ADCs may produce digital samples of eight, twelve or sixteen bits, for instance, and hence the digital signal value is expressed within the resolution determined by the number of bits into which the signal is resolved.

Figure 3:
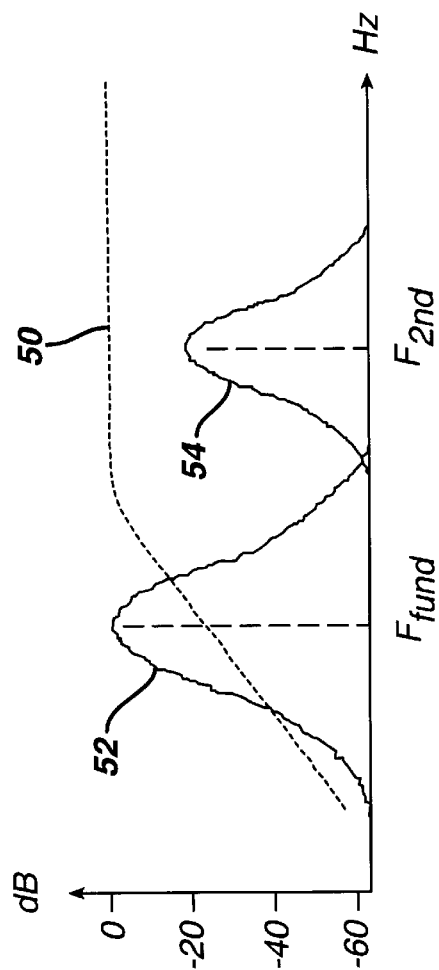
FIG. 3 illustrates the characteristic of a filter employed in accordance with the present invention overlaying fundamental and harmonic passbands.

The circuit 10 also includes two filter circuits 14 and 18. In accordance with the principles of the present invention the filter 14 is a highpass or bandpass filter with a lower cutoff or knee of the characteristic which is above the center of the fundamental frequency band $f_{fund}$. This filter characteristic, an example of which is illustrated by the dashed line 50 in FIG. 3, attenuates signals in the fundamental frequency band 52 in relation to signals in the second harmonic frequency band 54 centered about frequency $f_{2nd}$. The filter characteristic may be shaped to provide the desired degree of attenuation of fundamental frequency components. The lower frequency cutoff may only partially attenuate signals in the fundamental band 52 as illustrated by filter characteristic 50, or may provide a fuller cancellation of fundamental components by a steeper roll-off between the fundamental and harmonic bands. Preferably the filter roll-off should attenuate the fundamental components so that the levels of expected fundamental components in the received echo signals will be at or below the levels of the anticipated harmonic components. This will reduce the possibility of saturation of the ADC 115 when a significant portion of the dynamic range of the ADC is applied to the dynamic range of anticipated harmonic signals. This in turn will reduce the signal clipping that saturation produces and the resultant production of unwanted harmonic generation at the echo frequencies of interest. The matching of the harmonic signal dynamic range is controlled by the characteristics of the filters 14 and 18, and by the gain of the TGC 1 and 2 circuits. While the harmonic-enhancing filter 14 can be employed without the TGC circuits or filter 18, the use of filter 14 in concert with TGC control enables the system designer to balance tradeoffs between the TGC gain and the ADC saturation level. By reducing the possibility of ADC saturation in this manner, harmonic components may be more reliably detected. The sensitivity of the ultrasound system to harmonic signals is also improved, as the harmonic signal dynamic range can be distributed over a greater portion of the ADC dynamic range.

Figure 6:
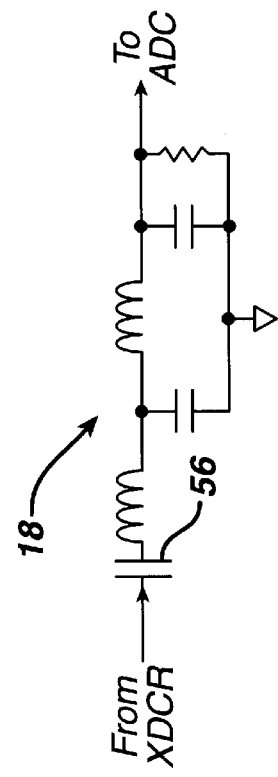
FIG. 6 illustrates the A/D filter of FIG. 4 schematic detail.

Preceding the ADC 115 is an anti-aliasing filter 18. The filter 18 is a highpass or bandpass filter which has an upper frequency cutoff below the sampling frequency $f_s$ of the ADC 115. The filter 18 thus prevents signals above the sampling frequency fs from being replicated or aliased down to the passband of interest by the sampling process. A typical anti-aliasing filter 18 is shown in FIG. 6. This filter is seen to have a series capacitance 56, which blocks DC. The filter 18 in FIG. 6 is a bandpass filter which can be tailored to have a high frequency cutoff below the ADC sampling frequency and a low frequency cutoff above DC and below the lowest frequency of the passbands of the transducers which are to be used with the ultrasound system.

Figure 4:
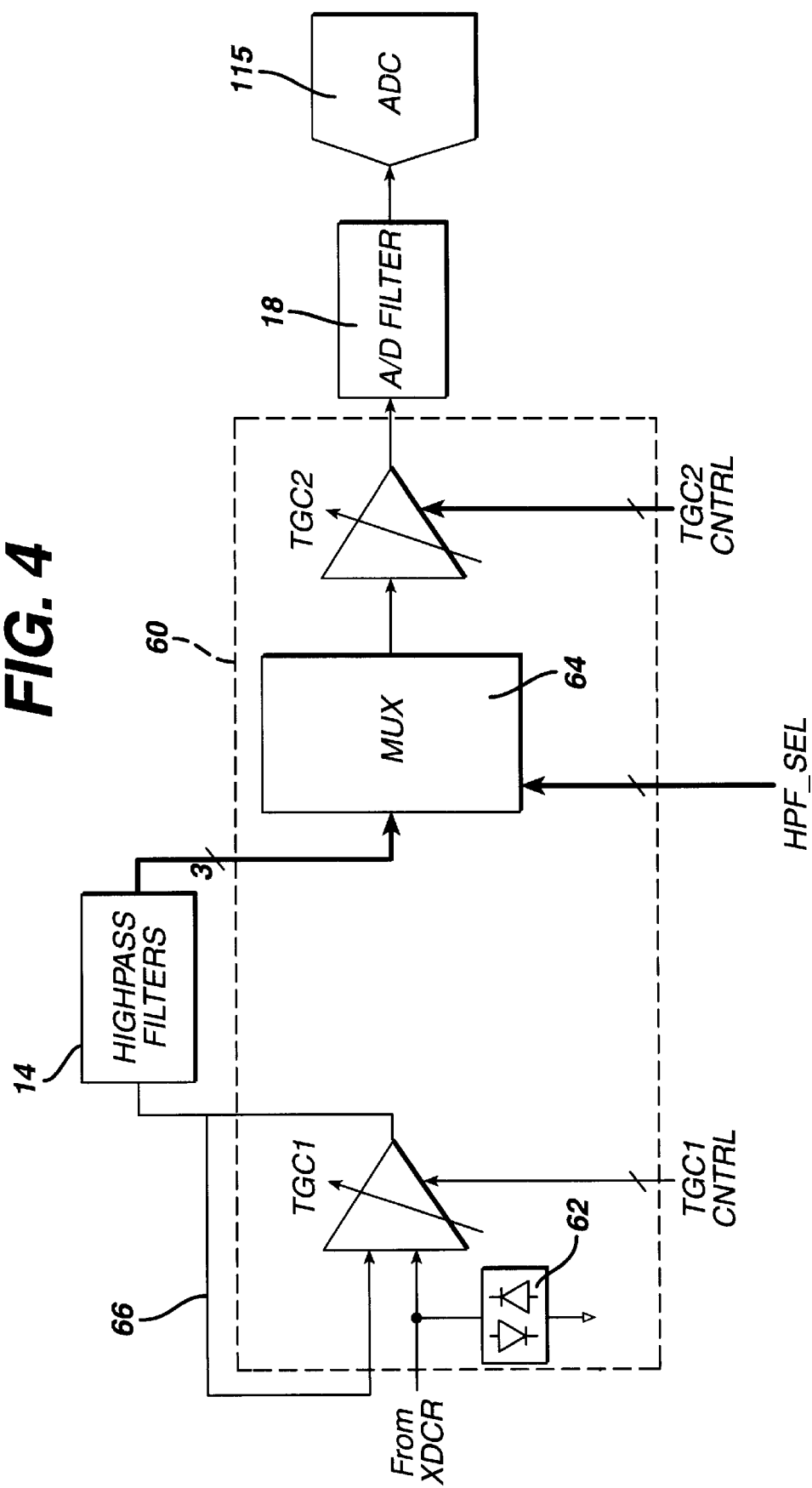
FIGS. 4 and 5 illustrate details of an interbreed circuit embodiment of the present invention.

FIG. 4 illustrates an embodiment of the acquisition circuit of FIG. 2 in which a number of the circuit components are realized in integrated circuit form. The dashed box 60 outlines components which are realized on a common integrated circuit chip in this embodiment. The TGC1 and TGC2 circuits are located on the integrated circuit chip 60, as is a multiplexer 64 The TGC1 circuit has an input to which the signal received by the transducer is applied. Clamp diodes 62 are connected in shunt with this input to protect the TGC input from the drive signal which is applied to the transducer during transmit. The gain of the TGC1 circuit is controlled by an externally applied TGC1 CNTRL signal during reception of echo signals. The TGC1 circuit has a second input which is shown connected as a feedback path 66. Since the feedback path is external to the chip 60, different discrete resistive and reactive components can be used co provide a selected feedback characteristic for a given ultrasound system.

Coupled external to the chip 60 between the output of the TCG1 circuit and the input to the multiplexer 64 is a bank of highpass filters 14. In this particular embodiment three highpass filters are used. The three filters are coupled to inputs of the multiplexer 64 which selects signals from the desired filter or filters under control of a HPF_SEL control signal. The selected signals are coupled to the input of the TGC2 circuit, the gain of which is controlled by a TGC2 CNTRL signal. The output o the TGC2 circuit is coupled to the A/D filter 18, which in turn is coupled to the input of the ADC 115.

Figure 5:
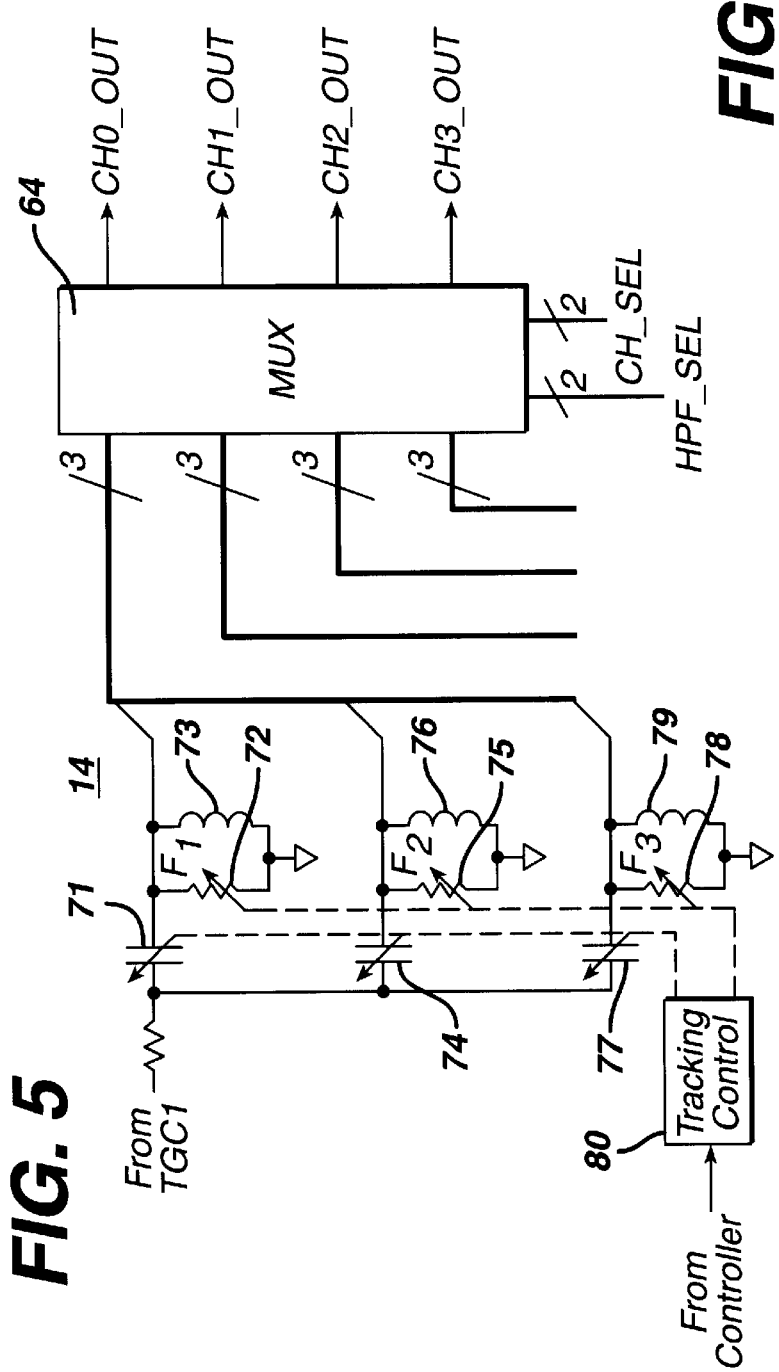

The filters 14 and multiplexer 64 are shown in greater detail in FIG. 5. The filters 14 in this embodiment comprise three highpass filters connected in parallel. Each filter includes a series capacitive component (71,74,77) and shunt resistive (72,75,78) and inductive (73,76,79) components chosen to provide the respective filters with the desired passband characteristics. In this embodiment the filters 14 are Butterworth filters with filter $F_1$ having a lower corner frequency of 1.5 MHz, filter $F_2$ having a lower corner frequency of 4.5 MHz, and filter $F_3$ having a lower corner frequency of 7.5 MHz. The three filters are coupled to three inputs of the multiplexer 64. The multiplexer 64 is also shown to have inputs for three other filter sets, thereby enabling the multiplexer to serve three other acquisition circuits for three other transducer elements connected to the chip 60. The multiplexer 64 thus has a second set of control inputs, CH_SEL, by which the signals from one or more transducer channels are selected and coupled to the outputs of the multiplexer.

There are a variety of ways in which the filters and multiplexer can be employed. In one embodiment one or more of filters $F_1$, $F_2$, or $F_3$ are selected by the multiplexer in correspondence with the passband of the transducer being used. When a high frequency transducer is used the multiplexer selects the 7.5 MHz filter in response to the transducer being selected. When a mid-frequency transducer is used the multiplexer selects the 4.5 MHz filter, and when a low frequency transducer is used the multiplexer selects the 1.5 MHz filter. The filters are thus switched into use in correspondence with the transducer being used. When the ultrasound system is used to produce images from only fundamental frequency signals the filters can be bypassed. Preferably, however, the lowest frequency filter $F_1$ is switched into use during fundamental signal imaging to pass a broad range of frequencies with the exception of low frequency noise which is eliminated by the $F_1$ filter cutoff.

Alternatively, in another embodiment the filters can be programmable. FIG. 5 illustrates filters with variable capacitive and resistive components, enabling one filter circuit to be programmed in correspondence with the received signal characteristics. A variable capacitance can be provided by an adjustably biased varactor diode, for instance, with the capacitance be set to the desired filter characteristic. One, two or all three filter components can be variable and hence programmable; the illustration of FIG. 5 shows the capacitive and resistive components being varied. In this alternative embodiment the characteristic of a filter is programmed in correspondence with the transducer being used.

In accordance with a further aspect of the present invention, the characteristic of the programmable or switchable filters can be dynamically varied during reception of echo signals to track the effects of depth dependent frequency attenuation. FIG. 5 illustrates a cracking control circuit 80 which is responsive to the central controller to vary the variable filter element or elements during reception of echo signals. As echoes are received from ever increasing depths following a pulse transmission, the bandwidth of useable harmonic signals will shift downward due to frequency dependent attenuation of higher frequencies. As it does, the characteristic of the filter or filters tracks lower also, under control of the tracking control circuit 80, which is synchronized with the transmission of a transducer transmit pulse. The low frequency cutoff can track lower to continually be below the center frequency of the harmonic band and above the center frequency of the fundamental band, for instance. At the same time, the high frequency cutoff can track lower to attenuate higher frequencies which become noise-filled at deeper depths. Either one or the other of the cutoffs can be controlled in this manner. Preferably, both are controlled simultaneously.

An alternative approach to tracking the effects of depth dependent frequency attenuation is to switch from a higher frequency filter to one or more lower frequency filters during echo reception. Rather than vary the characteristics of one filter, a series of filters are switched into the signal path in sequence. This switching can be performed by the multiplexer, which switches in another filter at the appropriate time during signal reception. Preferably the filters have overlapping characteristics so that a smooth transition occurs as the multiplexer switches from one filter to the next. Four, five, or a greater number of filters of decreasing center frequency can be switched in and out in this manner during echo reception. To smooth the transition from one filter to the next, a cross-fading control can be employed to decrease the signal from one filter and increase the signal from another as the transition is made from one filter to the next. As the use of one filter is ending its output response can be rolled down as the output response of the next filter in the sequence is rolled up. Thus, a switched system will smoothly transition from one filter to the next as echoes are received.

Depth dependent tracking can be employed when multizone imaging is performed by switching to a different filter for different depth zones. For example, a high frequency passband filter can be used during reception of a near field zone, followed by a mid frequency passband filter for a mid field zone and a low frequency passband during reception of a far field zone. Since the filters can be switched between reception intervals in multizone, the transient effects of filter switching or variation during reception are avoided.

The depth dependent gain control of the TGC circuits and the depth dependent frequency attenuation compensation both vary dynamically during echo reception as a function of depth. This means that the same or variations of the same timing control signal can be employed for both TGC control and frequency attenuation tracking control on the chip 60 including the filters 14. The use of a commonly derived control characteristic can thus minimize the connections to the acquisition circuit and/or the integrated circuit chip 60 and filters 14.

What is claimed is:

1. An ultrasonic diagnostic imaging system comprising:
   a transducer which receives ultrasonic echo signals containing fundamental and harmonic signal components;
   a frequency sensitive circuit, coupled to receive echo signals produced by said transducer, which passes harmonic frequency signal components relative to fundamental frequency signal components;
   an analog to digital converter coupled to receive echo signals processed by said frequency sensitive circuit; and
   a digital beamformer coupled to receive digital echo signals produced by said analog to digital converter.

2. The ultrasonic diagnostic imaging system of claim 1, wherein said frequency sensitive circuit comprises an attenuating circuit that exhibits a passband which attenuates fundamental signal components relative to harmonic signal components.

3. The ultrasonic diagnostic imaging system of claim 2, wherein said passband exhibits a lower corner frequency which is above a given fundamental signal frequency and below the second harmonic of said given fundamental signal frequency.

4. The ultrasonic diagnostic imaging system of claim 3, wherein said fundamental signal components occupy a fundamental signal passband and said harmonic signal components occupy a harmonic signal passband; and
   wherein said corner frequency is above the center frequency of said fundamental signal passband and below the center frequency of said harmonic signal passband.

5. The ultrasonic diagnostic imaging system of claim 1, wherein said frequency sensitive circuit comprises a highpass filter.

6. The ultrasonic diagnostic imaging system of claim 5, wherein said highpass filter exhibits a passband having a lower corner frequency which is above a given fundamental signal frequency and below the second harmonic of said given fundamental signal frequency.

7. The ultrasonic diagnostic imaging system of claim 1, wherein said frequency sensitive circuit comprises a bandpass filter.

8. The ultrasonic diagnostic imaging system of claim 7, wherein said bandpass filter exhibits a passband having a lower corner frequency which is above a given fundamental signal frequency and below the second harmonic of said given fundamental signal frequency, and said passband includes said second harmonic frequency.

9. The ultrasonic diagnostic imaging system of claim 1, wherein the transducer further comprises an array transducer having a plurality of transducer elements which receive ultrasonic echo signals containing fundamental and harmonic signal components;
   wherein the digital beamformer further comprises a digital beamformer having a plurality of processing channels coupled to receive ultrasonic echo signals from respective ones of said transducer elements;
   wherein the analog to digital converter further comprises a plurality of analog to digital converters having outputs coupled to respective ones of said digital beamformer processing channels; and
   wherein the frequency sensitive circuit further comprises a plurality of attenuating circuits coupled between said transducer elements and said analog to digital converters which attenuate fundamental signal components to a greater degree than harmonic signal components.

10. The ultrasonic-diagnostic imaging system of claim 9, wherein said attenuating circuits comprise highpass filters.

11. The ultrasonic diagnostic imaging system of claim 9, wherein said attenuating circuits comprise bandpass filters.

12. The ultrasonic diagnostic imaging system of claim 1, wherein the frequency sensitive circuit further comprises a circuit, coupled to receive echo signals produced by said transducer, which enhances harmonic signal components relative to fundamental frequency signal components.

13. The ultrasonic diagnostic imaging system of claim 12, wherein the frequency sensitivity of said frequency sensitive circuit is programmable.

14. An ultrasonic diagnostic imaging system comprising:
   a transducer which receives ultrasonic echo signals containing fundamental and harmonic signal components;
   a frequency sensitive circuit, coupled to receive echo signals produced by said transducer, which passes harmonic frequency signal components relative to fundamental frequency signal components;
   an analog to digital converter coupled to receive echo signals processed by said frequency sensitive circuit; and
   digital echo signal processor coupled to receive digital echo signals produced by said analog to digital converter;
   wherein the frequency sensitive circuit further comprises a circuit, coupled to receive echo signals produced by said transducer, which enhances harmonic signal components relative to fundamental frequency signal components;
   wherein the digital echo signal processor further comprises a digital beamformer coupled to receive digital echo signals produced by said analog to digital converter;
   wherein said analog to digital converter is operated at a sampling frequency; and
   further comprising a second frequency sensitive circuit, coupled between said transducer and said analog to digital converter, which attenuates signals at said sampling frequency.

15. The ultrasonic diagnostic imaging system of claim 14, wherein said first frequency sensitive circuit comprises a filter circuit having a maximum response above a fundamental frequency; and
   wherein said second frequency sensitive circuit comprises an anti-aliasing filter.

16. An ultrasonic diagnostic imaging system comprising:
   a transducer which receives ultrasonic echo signals containing fundamental and harmonic signal components;
   a frequency sensitive circuit, coupled to receive echo signals produced by said transducer, which passes harmonic frequency signal components relative to fundamental frequency signal components;
   an analog to digital converter coupled to receive echo signals processed by said frequency sensitive circuit; and
   a digital echo signal processor coupled to receive digital echo signals produced by said analog to digital converter;
   wherein the frequency sensitive circuit further comprises a circuit, coupled to receive echo signals produced by said transducer, which enhances harmonic signal components relative to fundamental frequency signal components;
   wherein the digital echo signal processor further comprises a digital beamformer coupled to receive digital echo signals produced by said analog to digital converter;

wherein said frequency sensitive circuit comprises a plurality of selectable circuits of different frequency sensitivity.

17. An ultrasonic diagnostic imaging system comprising:
a transducer which receives ultrasonic echo signals containing fundamental and harmonic signal components;
a frequency sensitive circuit, coupled to receive echo signals produced by said transducer, which passes harmonic frequency signal components relative to fundamental frequency signal components;
an analog to digital converter coupled to receive echo signals processed by said frequency sensitive circuit; and
a digital echo signal processor coupled to receive digital echo signals produced by said analog to digital converter;
wherein the transducer comprises a transducer which receives ultrasonic echo signals containing fundamental and harmonic signal components at given frequencies;
wherein the frequency circuit further comprises a plurality of tuned circuits, coupled to receive said echo signals, which are tuned to pass harmonic signals of different frequencies;
wherein the analog to digital converter is coupled to receive echo signals passed by said tuned circuits;
further comprising a tuned circuit selector, coupled to said tuned circuits, which selectively enables passage of harmonic signals by one of said tuned circuits to said analog to digital converter; and
wherein the digital echo signal processor further comprises a digital beamformer coupled to receive digital echo signals produced by said analog to digital converter.

18. The ultrasonic diagnostic imaging system of claim 17, wherein said tuned circuit selector comprises a multiplexer.

19. The ultrasonic diagnostic imaging system of claim 17, wherein said transducer exhibits a nominal operating frequency; and
wherein said tuned circuit selector acts to enable passage of harmonic signals in correspondence with said nominal operating frequency.

20. The ultrasonic diagnostic imaging system of claim 17, wherein said tuned circuit selector acts to enable passage of harmonic signals in correspondence with depth dependent attenuation effects.

21. The ultrasonic diagnostic imaging system of claim 17, wherein said tuned circuit control acts to enable passage of harmonic signals by said variable tuned circuit in correspondence with depth dependent attenuation effects.

22. An ultrasonic diagnostic imaging system comprising:
a transducer which receives ultrasonic echo signals containing fundamental and harmonic signal components;
a frequency sensitive circuit, coupled to receive echo signals produced by said transducer, which passes harmonic frequency signal components relative to fundamental frequency signal components;
an analog to digital converter coupled-to receive echo signals processed by said frequency sensitive circuit; and
a digital echo signal processor coupled to receive digital echo signals produced by said analog to digital converter;
wherein the transducer further comprises a transducer which receives ultrasonic echo signals containing fundamental and harmonic signal components at given frequencies;
wherein the frequency sensitive circuit further comprises a variable tuned circuit, coupled to receive said echo signals, which is variably tuned to pass harmonic signals relative to corresponding fundamental frequencies;
wherein the analog to digital converter is coupled to receive echo signals passed by said variable tuned circuit;
further comprising a tuned circuit control, coupled to said variable tuned circuit, which selectively tunes said variable tuned circuit to pass harmonic signals of a desired frequency; and
wherein the digital echo signal processor further comprises a digital beamformer coupled to receive digital echo signals produced by said analog to digital converter.

23. The ultrasonic diagnostic imaging system of claim 22, wherein said variable tuned circuit comprises one or more variable resistive or reactive components coupled to said tuned circuit control.

* * * * *